(12) United States Patent
Kingston et al.

(10) Patent No.: US 11,821,852 B2
(45) Date of Patent: Nov. 21, 2023

(54) METHOD OF INVESTIGATING A SPECIMEN USING A TOMOGRAPHIC IMAGING APPARATUS

(71) Applicant: FEI Company, Hillsboro, OR (US)

(72) Inventors: Andrew M. Kingston, Kambah (AU); Shane Latham, Griffith (AU); Adrian Sheppard, Fisher (AU); Glenn Myers, Waramanga (AU); Trond Karsten Varslot, Vuku (NO)

(73) Assignee: FEI Company, Hillsboro, OR (US)

( * ) Notice: Subject to any disclaimer, the term of this patent is extended or adjusted under 35 U.S.C. 154(b) by 266 days.

(21) Appl. No.: 17/490,261

(22) Filed: Sep. 30, 2021

(65) Prior Publication Data
US 2022/0099600 A1    Mar. 31, 2022

(30) Foreign Application Priority Data
Sep. 30, 2020   (EP) ..................................... 20199128

(51) Int. Cl.
*G01N 23/00*     (2006.01)
*G01N 23/046*    (2018.01)
*G06T 11/00*     (2006.01)

(52) U.S. Cl.
CPC .......... *G01N 23/046* (2013.01); *G06T 11/008* (2013.01); *G01N 2223/418* (2013.01)

(58) Field of Classification Search
CPC ............ G01N 2223/418; G01N 23/046; G06T 11/008
See application file for complete search history.

(56) References Cited

U.S. PATENT DOCUMENTS

| | | |
|---|---|---|
| 2006/0198491 A1 | 9/2006 | Taguchi |
| 2017/0172525 A1 | 6/2017 | Proksa |
| 2017/0330724 A1* | 11/2017 | Okumura ................ H01J 37/22 |

FOREIGN PATENT DOCUMENTS

EP    3133554    2/2017

OTHER PUBLICATIONS

Abbas Sajid et al, Effects of sparse sampling schemes on image quality in low-dose CT, Medical Physics, AIP, Melville, NY, US, vol. 40, No. 11, Nov. 2013.

(Continued)

*Primary Examiner* — Dani Fox

(57) ABSTRACT

A method of investigating a specimen using tomographic imaging, comprising the steps of providing a specimen and a source, directing a beam of radiation from said source to said specimen, and detecting a flux of radiation transmitted through said specimen. The method further comprises the steps of moving at least one of said specimen and said source for providing relative motion of the source with respect to the specimen; and imaging the specimen along a series of different viewing axes, which intersect a virtual reference surface that surrounds the specimen and is substantially centered thereon, wherein said combined steps of moving and imaging generate a sampling geometry on said virtual reference surface. As defined herein, the steps of moving and imaging are coordinated in such a way that said sampling geometry comprises a plurality of spaced apart line segments.

20 Claims, 7 Drawing Sheets

(56) References Cited

OTHER PUBLICATIONS

Kudo H et al, New approximate filtered backprojection algorithm for helical cone-beam CT with redundant data, 2003 IEEE Nuclear Science Symposium Conference Record. / 2003 IEEE Nuclear Science Symposium and Medical Imaging Conference. Portland, OR, Oct. 19-25, 2003; [IEEE Nuclear Science Symposium Conference Record], New York, NY: IEEE, US, Oct. 19, 2003, pp. 3211-3215.
EP Search Report dated Mar. 15, 2021, EP Application No. 20199128.8, Filed Sep. 30, 2021.

* cited by examiner

METHOD OF INVESTIGATING A SPECIMEN USING A TOMOGRAPHIC IMAGING APPARATUS

FIELD OF THE INVENTION

The invention relates to methods and systems of investigating a specimen using a tomographic imaging apparatus, as well as a charged-particle microscope provided with such a tomographic imaging apparatus.

BACKGROUND OF THE INVENTION

In tomographic imaging (also referred to as Computed Tomography (CT)) as referred to above, the source and (diametrically opposed) detector are used to look through the specimen along different lines of sight (viewing axes), so as to acquire penetrative observations of the specimen from a variety of perspectives; these are then used as input to a mathematical procedure that produces a reconstructed "volume image" of (part of) the (interior of) the specimen. In order to achieve a series of different lines of sight as alluded to here, one can, for example, choose to:
  (a) Keep the source and detector static and move the specimen relative to them;
  (b) Keep the specimen static and move the source relative to it. In this case, one can elect to:
    Move the detector in synchronization with the source; or
    Embody the detector as a (static) array of sub-detectors, with positions matched to correspond to the different positions to be assumed by the source.

Regardless of whether the source or specimen is moved, it is possible to describe their relative motion using (for example) a specimen-centric coordinate system or reference frame. The beam of radiation that traverses the specimen and is received by the detector can, for example, be regarded as being cone-like (thus yielding so-called cone beam tomography) for a substantially 2D detector, or resembling a segment of a disc (thus yielding so-called fan beam tomography) for a substantially 1D detector. The associated viewing axis alluded here is regarded as corresponding to an optical axis along which the beam (from source through specimen to detector) propagates; it basically corresponds to the position of a central ray in that beam. In order to achieve sufficient sample penetration, the employed radiation will generally comprise X-rays.

Tomographic imaging as referred to here can be performed using a standalone apparatus, which is conventionally the case in medical imaging applications, for example, where the specimen (e.g. a human or animal) is macroscopic. Standalone CT tools are also available for performing so-called "micro CT", in which a micro-focused source is used to image microscopic specimens, e.g. in geology/petrology, biological (tissue or pharmacological) studies, etc. Continuing this drive toward ever-greater resolution, so-called "nano CT" instruments have also been developed; these may be standalone tools, but, for example, they may also be embodied as add-on modules for a charged-particle microscope (CPM), in which case the CPM's charged-particle beam can be used to irradiate a metal target, causing production of the Bremsstrahlung X-rays used to perform the desired tomography. The use of charged particles for performing the desired tomography is conceivable as well. The disclosure is not limited to X-ray tomography, but includes other types of tomography, such as electron tomography, as well.

It should be noted that, as referred to here in the context of a CPM, the phrase "charged particle" should be broadly construed as encompassing:
  Electrons, as in the case of a Transmission Electron Microscope (TEM), Scanning Electron Microscope (SEM), and Scanning Transmission Electron Microscope (STEM), for instance;
  Ions, which may be positive (e.g. Ga or He ions) or negative. Such ion beams can be used for imaging purposes, but they are also often used for surface modification purposes, e.g. as in the case of Focused Ion Beam (FIB) milling, Ion-Beam-Induced Deposition (IBID), Ion-Beam-Induced Etching (IBIE), etc.;
  Other charged particles, such as protons and positrons, for instance.

It should also be noted that, in addition to imaging and/or surface modification, a charged particle beam in a CPM may also have other functionalities, such as performing spectroscopy, and/or examining diffractograms.

As regards the relative motion between the specimen and the source employed to achieve different lines of sight, use is conventionally made of:
  A circular scan, in which the source follows a planar orbit about the specimen, and images are captured at a relatively high sampling rate (i.e. quasi-continuously) along this orbit. This type of scan can be applied in situations where only a relatively thin "slice" of a specimen has to be imaged, e.g. when making a cone beam CT scan of human dentition;
  A helical scan, in which the source follows a coil-like (spiral) path about a (longitudinal) axis of the specimen, and images are again captured at a relatively high sampling rate (i.e. quasi-continuously) along this path. This type of scan can be applied in situations where a relatively elongated portion of a specimen has to be imaged, e.g. when making a CT scan of (a portion of) a human vertebral column. It is typically achieved by combining circular motion (e.g. of the source) and concurrent translational motion (e.g. of the specimen);
  As an alternative to conventional curvilinear scan loci—such as the circular/spiral scan paths just referred to—one can, for example, also make use of a lattice-like data acquisition locus, e.g. as set forth in European Patent EP 3 133 554 B1.

Although prior-art techniques such as these have produced tolerable results up to now, the current inventors have worked extensively to provide an innovative alternative to the conventional approach. The results of this endeavor are the subject of the current invention.

It is an object of the invention to provide an innovative tomographic imaging technique, and more specifically, it is an object of the invention to provide faster acquisition times, whilst maintaining the same level of acquired data.

SUMMARY OF THE INVENTION

In one example, a method of investigating a specimen using tomographic imaging comprises providing a specimen and a source; directing a beam of radiation from said source to said specimen; detecting a flux of radiation transmitted through said specimen; moving at least one of said specimen and said source for providing relative motion of the source with respect to the specimen; and imaging the specimen along a series of different viewing axes, which intersect a virtual reference surface that surrounds the specimen and is substantially centered thereon, wherein said combined steps of moving and imaging generate a sampling geometry on said virtual reference surface; characterized in that said steps of moving and imaging are coordinated in such a way that said sampling geometry comprises a plurality of spaced apart line segments.

In another example, a tomographic imaging apparatus comprises a specimen holder for holding the specimen; a source for producing a beam of radiation that can be directed at the specimen; a detector for detecting a flux of radiation transmitted through the specimen from the source; a stage apparatus, for producing relative motion of the source with respect to the specimen, so as to allow the source and detector to image the specimen along a series of different viewing axes, which intersect a virtual reference surface that surrounds the specimen and is substantially centered thereon, thereby generating a sampling geometry; and controller for controlling operations of said tomographic imaging apparatus to execute the method disclosed herein.

DETAILED DESCRIPTION

Figure 1:
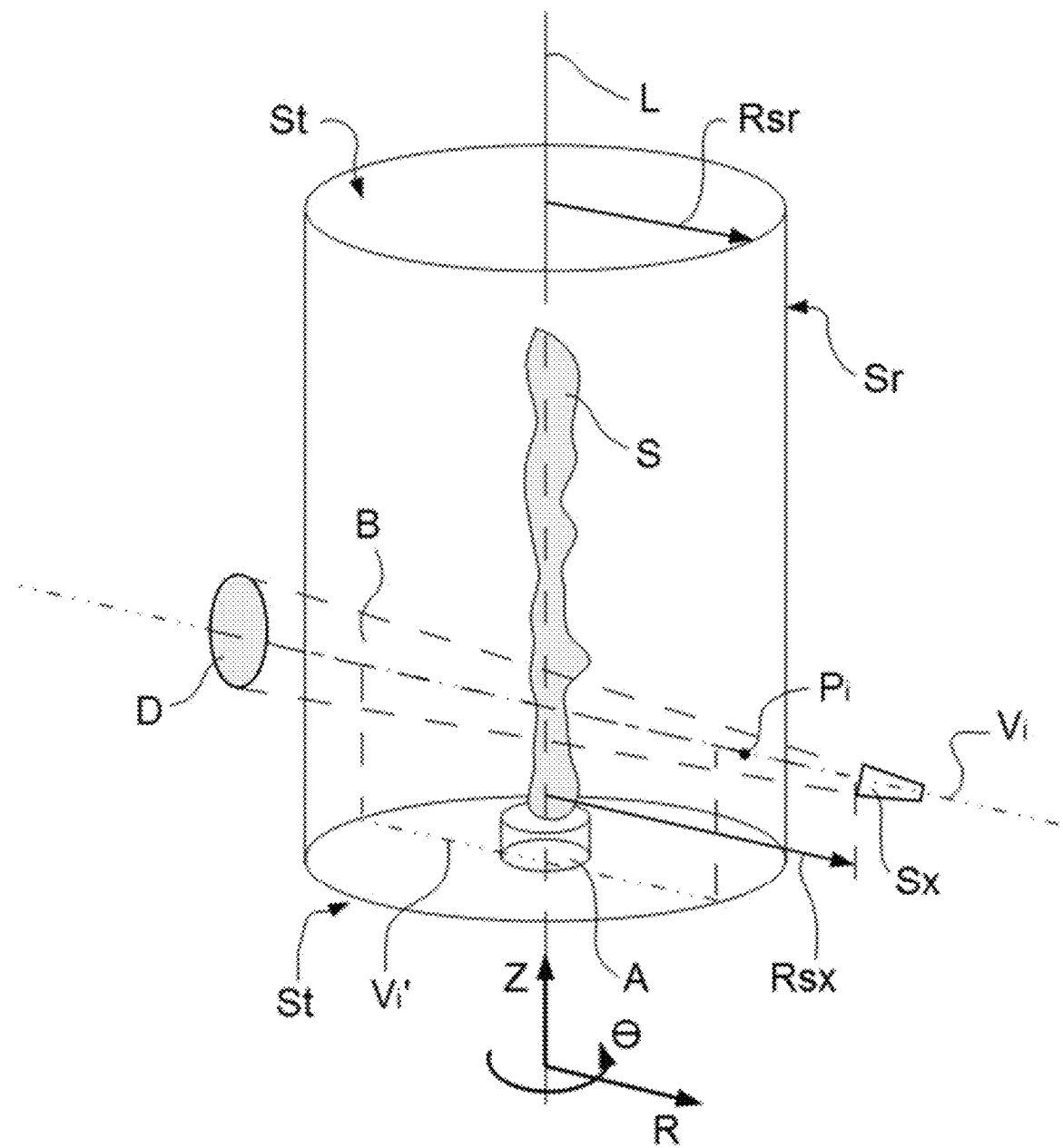
FIG. 1 renders a perspective view of a specimen undergoing tomographic imaging, and serves to explain certain (reference) geometric aspects of the current invention.

According to a method, a specimen and a source are provided, and a beam of radiation is directed from said source to said specimen. A flux of radiation transmitted through said specimen is detected. At least one of said specimen and said source is moved for providing relative motion of the source with respect to the specimen. The specimen may thus be imaged a series of different viewing axes, which intersect a virtual reference surface that surrounds the specimen and is substantially centered thereon. An incoming point of intersection of each of said viewing axes may be considered with this reference surface, and this way a set of such intersection points corresponding to said series of viewing axes may be generated. The combined steps of moving and imaging generate a sampling geometry on said virtual reference surface. The sampling geometry in effect comprises the set of intersection points corresponding to the series of viewing axes.

As defined herein, the steps of moving and imaging are coordinated in such a way that said sampling geometry comprises a plurality of spaced apart line segments. In this regard, a single line segment as defined herein is formed by a plurality of intersection points that are located next to each other, in such a way that a (virtual) line segment is created by the associated set of intersection points. The intersection points within a single line segment are positioned relatively close to each other, in such a way that continuous relative motion, e.g. continuous detector motion, can be used. For example, adjacent intersection points may have a center-to-center distance that is in between one to three times the diameter of a single intersection point, effectively forming a virtual line segment. The intersection points within a single line segment may, alternatively, be partially overlapping, i.e. the intersection points having a center-to-center distance that is less than one time the diameter of a single intersection point, effectively forming a true line segment. The virtual and true line segments allow continuous relative motion to be used.

The distance between adjacent line segments is relatively large, i.e. with adjacent line segments having a distance that is at least substantially larger than the distance between intersection points within a single line segment. The distance between the neighboring line segments may be in the order of a half a single line segment length or more, for example larger than two line segment lengths, such as for example more than five line segment lengths. Larger inter-line segment distances are conceivable as well.

The line segment comprises a plurality of intersection points, wherein the number of intersection points within a single line segment may lie in between 3 to 30, more preferably in between 5 and 20, such as for example 10 or 15.

By using a plurality of disjoint segments, a novel and inventive type of scanning trajectory is provided, that can be used, for example, in cone beam tomography. Within each line segment, the spacing between views (i.e. the spacing between intersection points) is small enough to allow continuous relative motion, e.g. continuous detector motion. The effect of between-segment gaps on image quality can be minimized, in embodiments, by distributing the segments uniformly on the 2D space of viewing directions so as to maximize data sufficiency. The trajectory as defined herein allows scanning at speeds close to those possible with continuous trajectories while also providing a far more complete coverage of the space of possible views, akin to lattice-sampling (point-wise) trajectories.

Conventional Space Filling Trajectories (SFT) is described in EP 3 133 554 B1, which is herein incorporated by reference. SFT wastes 90% of the scan time in motion. The multi-segment trajectory as disclosed herein reduces this to 50% by taking fewer, larger steps. The time to acquire a full scan with the trajectory as disclosed herein is reduced, compared to helical trajectories, from 15 minutes to 3 minutes, with no reduction in acquired data. If each segment comprises N images (i.e. N intersection points), then compared to SFT, motion occurs N times less frequently; segment spacing increases by $\sqrt{N}$ for uniform distribution in z-theta space and since acceleration-limited motion over a space s scales with $\sqrt{s}$; this combines to give a change in motion time of $$\frac{\sqrt{\sqrt{N}}}{N} = N^{-3/4}.$$

For a typical N of 10 this yields 6× reduction in motion time compared to the SFT. In practice, a 5× to 10× reduction in motion time can be obtained. Thus, from the above it follows that a faster acquisition is possible, with no reduction in acquired data, and with this the objective as defined herein is achieved.

Advantageous embodiments are subject to the dependent claims and will be discussed below.

In an embodiment, the method comprises the step of continuously imaging at least one of said plurality of spaced apart line segments.

In an embodiment, the method comprises the step of discontinuing imaging in between said plurality of spaced apart line segments.

In an embodiment, the sampling geometry comprises an array of said spaced apart line segments. The spaced apart line segments may be selected and placed in such a way that the array consists of a regular grid of spaced apart line segments.

In an embodiment, the step of moving comprises combined movement in a longitudinal (z) direction and in a tangential (θ) direction.

In an embodiment, sequential spaced apart line segments exhibit a continuity in said longitudinal direction.

In an embodiment, sequential spaced apart line segments exhibit a discontinuity in said tangential direction.

In an embodiment, said discontinuity corresponds with a tangential rotation of approximately 30-90°, and more preferably in between 45-75°.

In an embodiment, for a single line segment, said movement in said longitudinal direction is ranged in between 1-5% of total sample height.

In an embodiment, for a single line segment (Ls), said movement in said tangential direction is ranged in between 5-25°.

According to an aspect, a tomographic imaging apparatus is provided, comprising:

A specimen holder, for holding the specimen;

A source, for producing a beam of radiation that can be directed at the specimen;

A detector, for detecting a flux of radiation transmitted through the specimen (S) from the source;

A stage apparatus, for producing relative motion of the source with respect to the specimen, so as to allow the source and detector to image the specimen along a series of different viewing axes, which intersect a virtual reference surface that surrounds the specimen and is substantially centered thereon, thereby generating a sampling geometry; and A controller for controlling operations of said tomographic imaging apparatus.

The tomographic imaging apparatus as defined herein is arranged for executing the method as defined herein.

According to an aspect, a charged particle microscope is provided, comprising a tomographic imaging apparatus as defined herein.

FIG. 1 renders a perspective view of a specimen S undergoing tomographic imaging, and serves to explain certain (reference) geometric aspects of the current invention. In the Figure, an elongated specimen S (which may be macroscopic, micron-scale, or nanometer-scale, for example) has an associated longitudinal axis L. A radiation source Sx produces a beam B of radiation (typically X-rays) that propagates along an axis Vi, towards the detector D, which may be regarded as a viewing axis or line of sight. As here illustrated, Vi is substantially normal to longitudinal axis L. Having traversed a portion of the specimen S, the beam B impinges upon a (diametrically opposed) detector D, which may, for example, be a Silicon Drift Detector (SDD), Silicon Lithium (Si(Li)) detector, a pixelated detector, or other suitable detector. The beam may be defined by the locations of the detector and the source, as well as the geometries of the detector and the source. The beam B may be regarded as being (for example) cone- or fan-shaped, depending on the effective shape that the detector D "presents" to the source Sx. The detector D forms an electronic image of said portion of the specimen S, which can be stored in an electronic memory. This procedure is then repeated for a series of different viewing axes Vi, allowing the specimen S to be viewed along different lines of sight; thereafter, the various images acquired in this manner are used as input to a mathematical reconstruction procedure to produce a tomogram. The various viewing axes Vi are achieved by employing a stage apparatus to produce relative motion between the source Sx and specimen S, e.g. by producing translational/rotational motion of the source Sx/detector D and/or the specimen S in a pre-determined way. Such stage apparatus may, for example, comprise one or more linear motors, piezoelectric actuators, stepper motors, voice coil motors, pneumatic/hydraulic actuators, etc., and can readily be tailored by the skilled artisan to suit the needs of a given setup. In the specific embodiment depicted here, stage apparatus A can translate/rotate specimen S relative to source Sx/detector D.

Also shown in the Figure is a virtual reference surface Sr, which, in this case, is a cylindrical surface whose cylindrical axis coincides with longitudinal axis L. This reference surface Sr has a radius Rsr, chosen to be less than or equal to the distance Rsx of the source Sx from the axis L. The viewing axis Vi intersects this reference surface Sr at intersection point Pi. Viewing axis Vi can be projected linearly along L, and the projected viewing axis Vi' runs across the virtual disc-shaped terminal surface St at the lower end of the surface Sr. Associated with the reference surface Sr is a cylindrical coordinate system (R, θ, Z). The set {Pi} of intersection points Pi corresponding to the abovementioned series of viewing axes Vi can be regarded as representing a "data acquisition locus", such as the circular or helical scanning path referred to above, or the lattice-like locus set forth in aforementioned patent application EP 3 133 554 B1, for example.

In FIGS. 2-4B, the reference surface Sr has been unfurled (unwound about L) so as to form a flat surface Sr', with associated planar Cartesian coordinate system (Y, Z), whereby one can take Y=θR.

Figure 2:
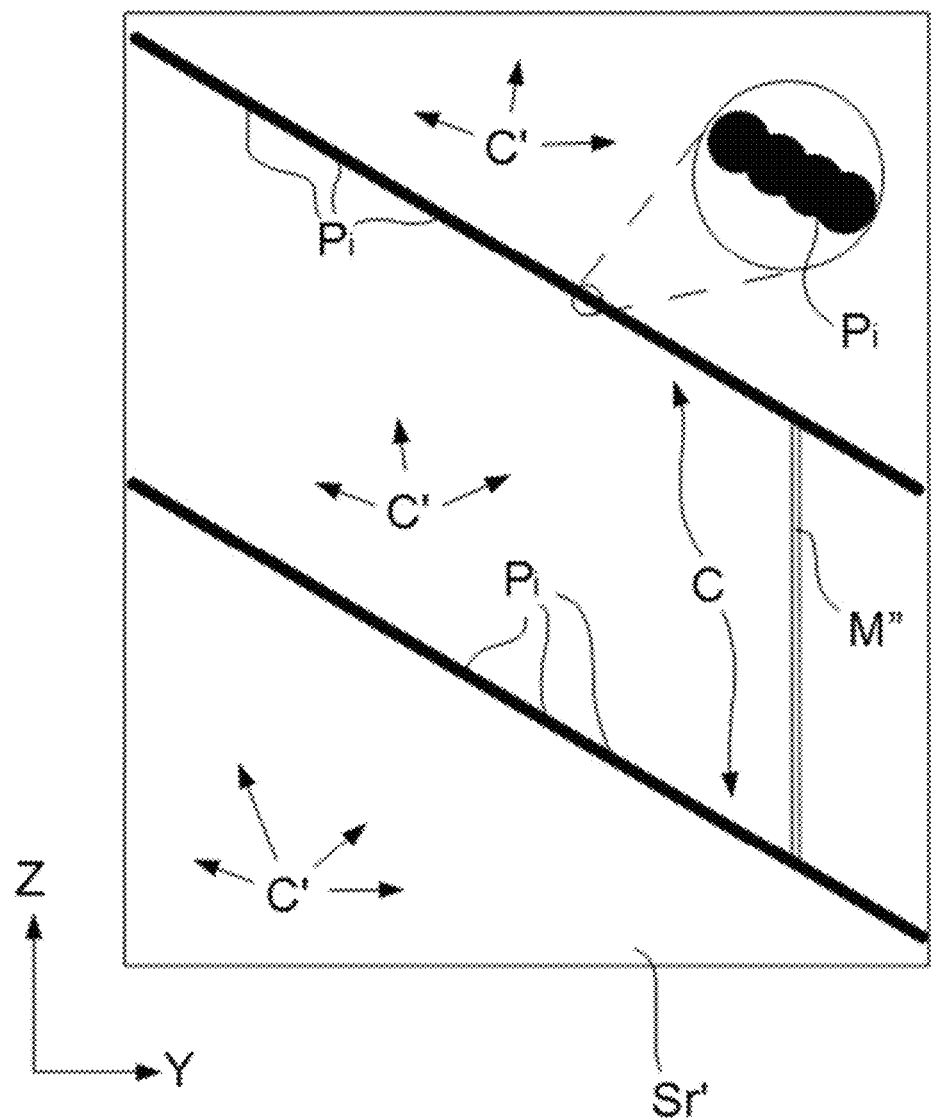
FIG. 2 renders a schematic overview of a prior-art tomographic trajectory, corresponding to a conventional helical scan.

Turning first to FIG. 2, this shows a prior-art situation corresponding to a conventional helical scan, in which the source Sx traces out a helical path relative to the axis L (by concurrently orbiting it about L, and displacing it parallel to L) and images are captured quasi-continuously (i.e. at a high sampling rate) along a succession of closely-separated viewing axes Vi. When the resulting helical path on reference surface Sr is unfurled, a result such as that shown in FIG. 2 is obtained, in which trains of closely-spaced intersection points Pi are located along (curvi-)linear tracts C (an exploded partial view at the top right of the Figure illustrates the close spacing of successive points Pi). The angle of attack of the helical path defines the distance M", as measured in the z-direction, between imaged points having the same Y-coordinate. Note the extreme lack of homogeneity/isotropy in this situation: there is a high concentration of points along tracts C (which are highly directional), and no points at all in the intervening regions C', as the distance M" is relatively high.

Figure 3:
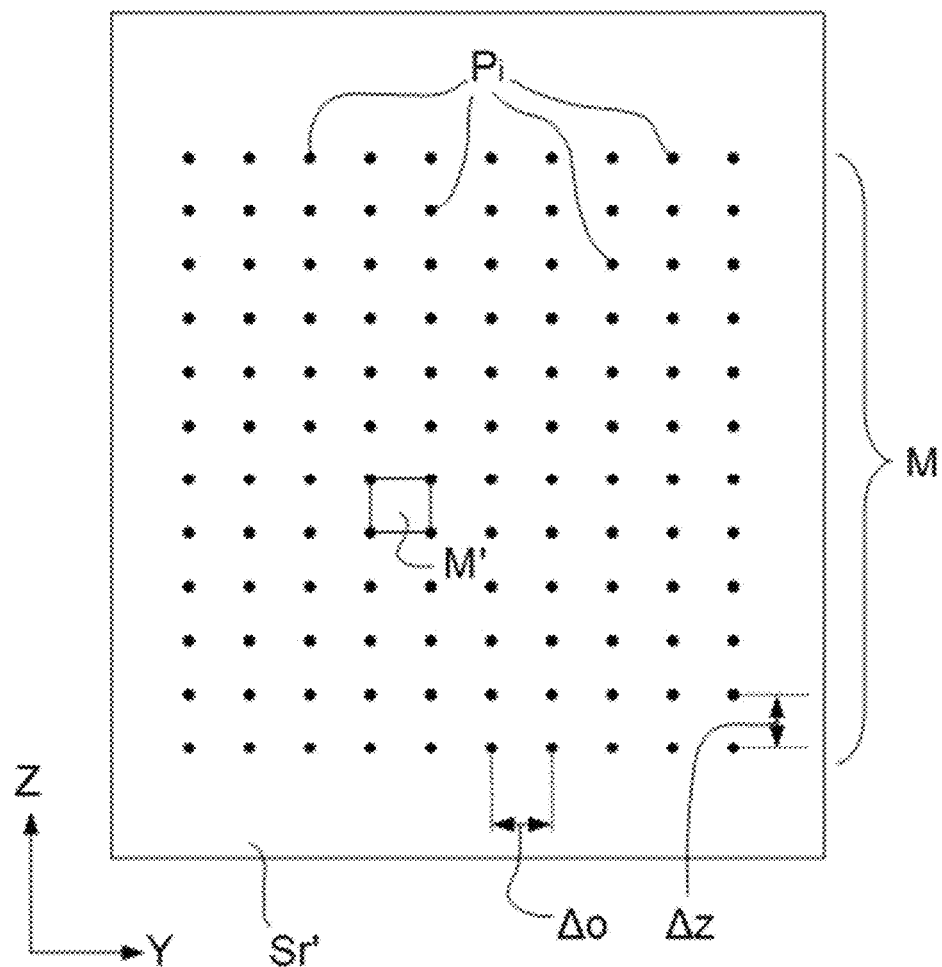
FIG. 3 renders a schematic overview of a prior-art tomographic trajectory, corresponding to a conventional matrix scan.

FIG. 3 shows a situation as described in EP 3 133 554 B1, wherein the relative motion of the source Sx and specimen S, and the attendant sampling (image-capture) frequency/intervals, are chosen so as to yield a two-dimensional lattice (matrix, net) M of points Pi located "areally" on (at least part of) surface Sr' in a substantially uniform distribution. Associated with this lattice M is a unit cell M', which can be regarded as a repeating fundamental "building block" of the lattice M. Neighboring points Pi have a distance Δo in the Y-direction, and Δz in the Z-direction. This sampling trajectory introduced a highly optimised 'space filling' scanning trajectory consisting of viewing angles distributed evenly about the z-theta space of possible source position. This has produced excellent data, with outstanding results for a-posteriori correction of unplanned motion yielding ultra-sharp images of sub-micron resolution, and high-quality images from reduced data volumes. However, space filling trajectories require large movements (typically 5 degrees) between each viewing angle, so that fast scanning is limited by stage acceleration. This may lead to substantial delays in scanning time. As an example, for a total imaging time of 15 mins, a total of approximately 12 mins may be required for moving the stage to all the subsequent imaging positions.

Figure 4A:
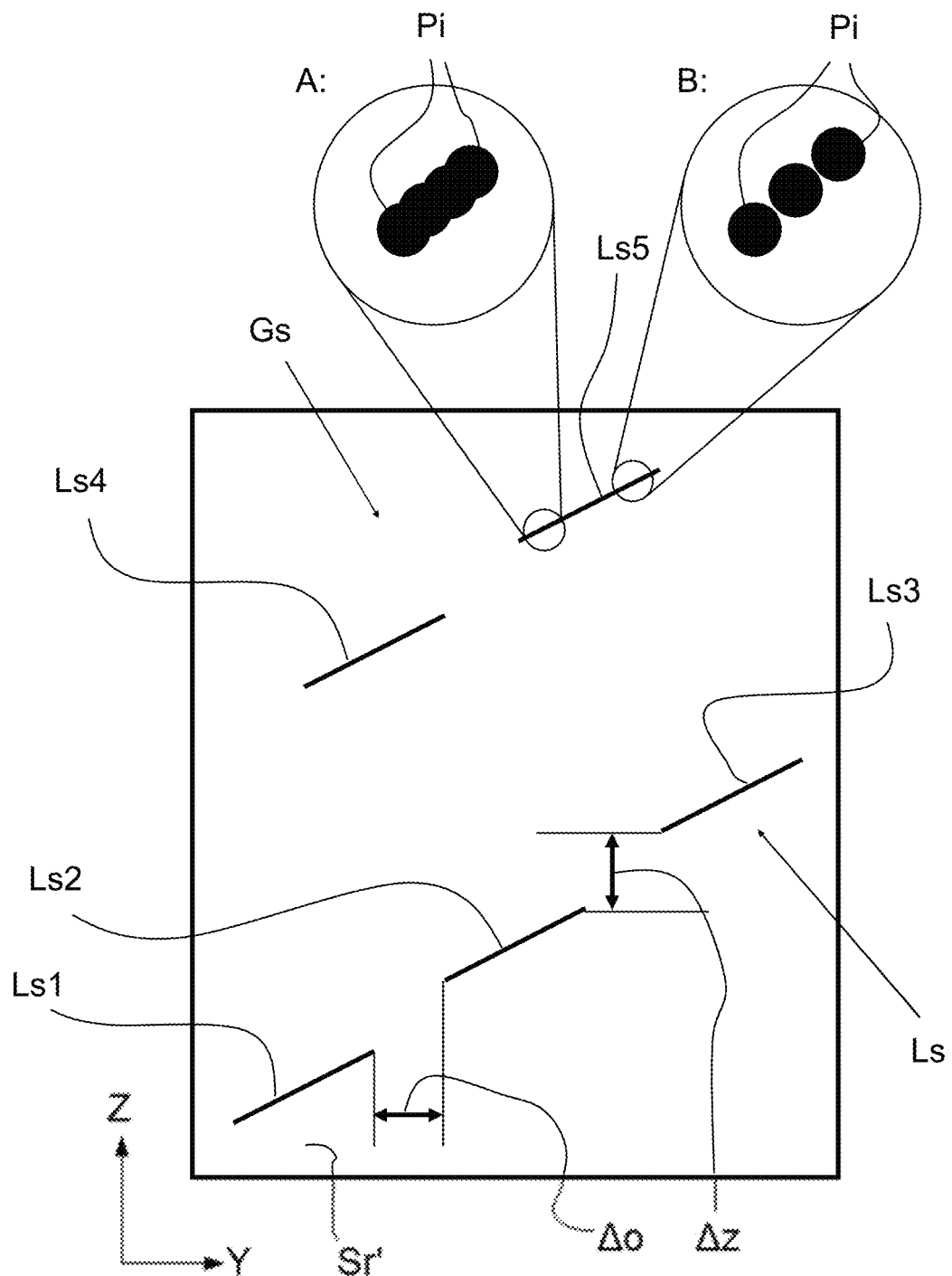
FIGS. 4a and 4b show schematic overviews of scanning trajectories according to the method as defined herein.
Figure 4B:
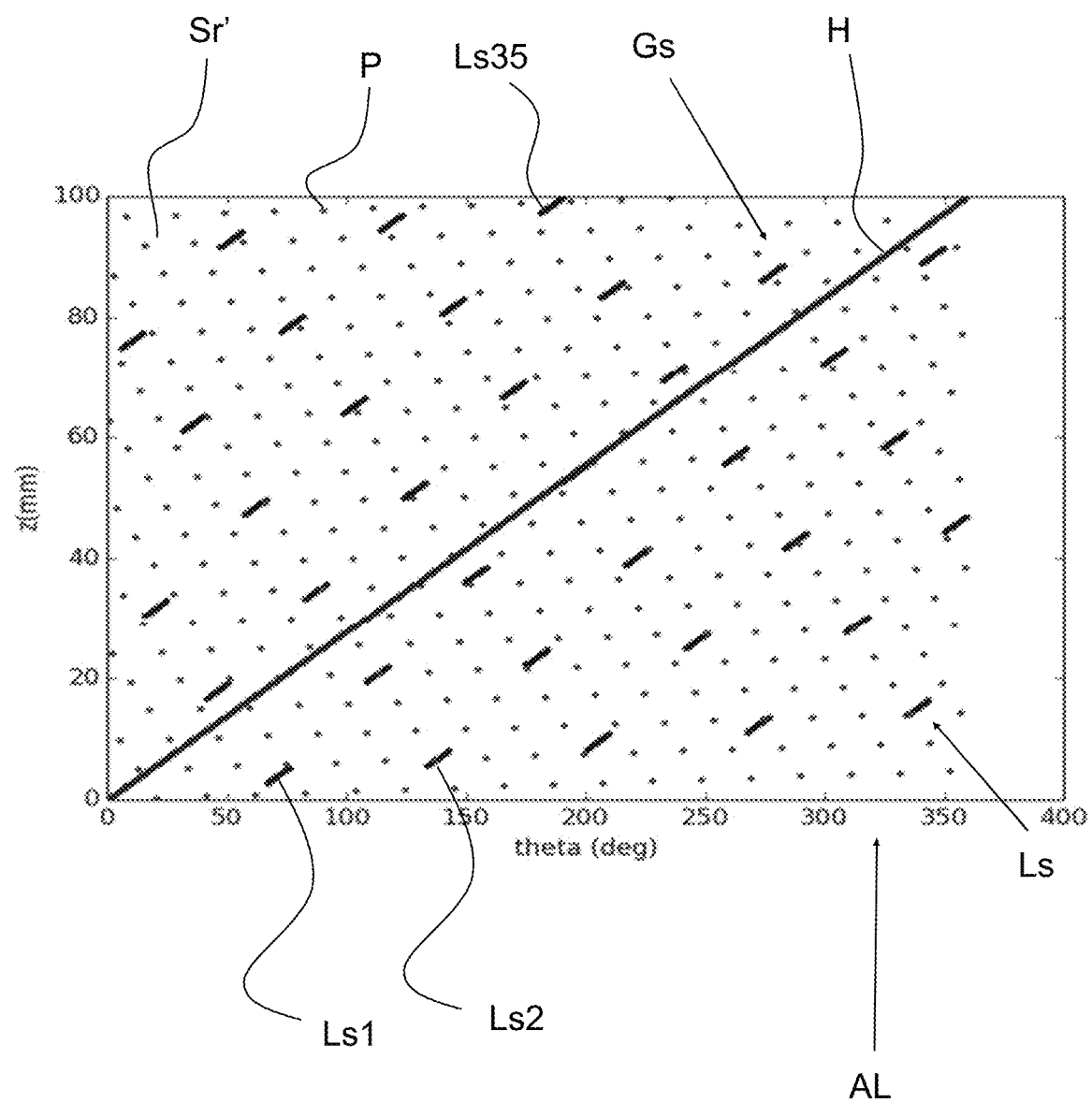

Now turning to FIGS. 4A and 4B, embodiments of scanning trajectories in line with the disclosure are shown.

FIG. 4A shows that the virtual reference surface Sr' comprises a sampling geometry Gs that comprises a plurality of spaced apart line segments Ls. Here, a total of five line segments Ls1-Ls5 are provided, that are spaced apart from each other. Each of the line segment Ls1-Ls5 comprises a number of intersection points Pi. Hence, each individual line segment Ls1-Ls5 comprises a plurality of intersection points Pi. The line segments may contain a total of 10 to 20 intersection points Pi, or even more, if desired. Neighboring intersection points Pi can show some overlap, as shown in inset "A" for line segment Ls5, such that the intersection points Pi are connected and a true line segment Ls5 is formed by the intersection points Pi. On the other hand, the intersection points Pi may also be placed apart from each other, as shown in inset "B" for line segment Ls5. This way, a virtual line segment is formed. In option "B", the distance between intersection points Pi may be in the order of one to three times the diameter of a single intersection point, effectively forming a virtual line segment, also be spaced apart from each other, by a relatively small distance, wherein the distance is in the order of the diameter of the intersection point Pi.

As shown in FIG. 4a, the second line segment Ls2 is spaced apart from the first line segment Ls1, in the Y-direction (tangential) by a distance Δo; and in the Z-direction (longitudinal) by a distance Δz. This way, an array of line segments Ls may be formed. The imaging trajectory shown in FIG. 4A is relatively fast, whilst maintaining the amount of acquired data.

Now turning to FIG. 4B, a comparison between the helical H scanning trajectory, the point-matrix P scanning trajectory, and the line segment Ls scanning trajectory as defined herein is shown. Here, it can be seen that the line segment Ls scanning trajectory is able to cover a wide area of the reference surface Sr'. By using line segments, a speed increase compared to the matrix P scanning trajectory is obtained, as movement and imaging may occur simultaneously.

The sampling geometry Gs shown in FIG. 4B effectively comprises an array AL of spaced apart line segments Ls. The array shown comprises a more or less regular grid of spaced apart line segments Ls, although a non-regular grid is conceivable as well. The line segments extend in both a longitudinal (z) direction and in a tangential (θ) direction. It is conceivable that the line segments extend only in the tangential direction, or only in the longitudinal direction. However, by extending in both the tangential and longitudinal direction, sample coverage is increased. The scanning trajectory as disclosed here improves data collection efficiency by collecting multiple closely-spaced views within each segment (requiring minimal motion), while also distributing the segments relatively uniformly through z-theta space to retain the main benefits of the SFT.

It can be seen in FIG. 4B, that the z-coordinate of the upper end of the first line segment Ls1 coincides with the z-coordinate of the lower end of the second line segment Ls2. Thus, the sequential spaced apart line segments (Ls) exhibit a continuity in said longitudinal z-direction. In between the first line segment Ls1 and the second line segment Ls2, a jump in the tangential coordinate takes place. Thus, sequential spaced apart line segments (Ls1-Ls2) exhibit a discontinuity in said tangential direction. In effect, the scanning trajectory as shown in FIG. 4B comprises longitudinal and tangential movement during imaging of the line segment, and comprises tangential movement only during movement from the first line segment Ls1 to the second line segment Ls2. This decreases the amount of required movement, and increases the speed with which the sample can be imaged.

The discontinuity in the tangential direction may correspond with a tangential rotation of approximately 30-90°, and more preferably in between 45-75°. For a single line segment (Ls), said movement in said longitudinal direction may be ranged in between 1-5% of the total height of the sample. For a single line segment (Ls), said movement in said tangential direction is ranged in between 5-25°. The total number of line segments used for imaging a specimen, may range in between 5 and 100. In the embodiment shown in FIG. 4B, the number of line segments is approximately 35. A higher number results in greater sample coverage.

Figure 5:
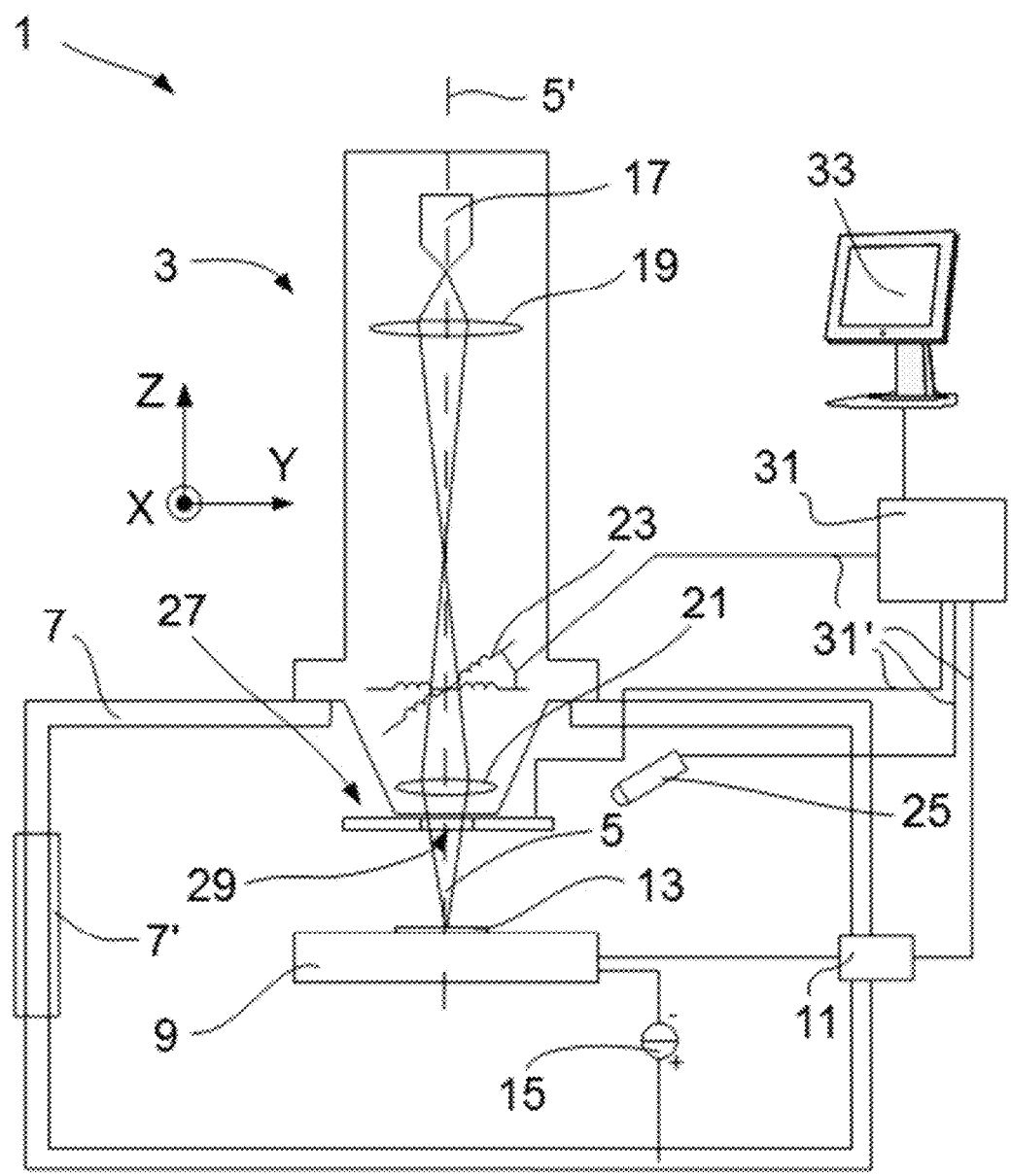
FIG. 5 renders a longitudinal cross-sectional elevation of a particular type of CPM in which an embodiment of the current invention can be carried out using a CT module.

FIG. 5 is a highly schematic depiction of an embodiment of a CPM 1 that can be used in conjunction with the present invention; more specifically, it shows an embodiment of a SEM—though, in the context of the current invention, it could just as validly be an ion-based microscope, for example, or a TEM, for instance. The microscope 1 comprises a particle-optical column/illuminator 3, which produces a beam 5 of charged particles (in this case, an electron beam) that propagates along a particle-optical axis 5'. The particle-optical column 3 is mounted on a vacuum chamber 7, which comprises a specimen holder 9 and associated stage/actuator 11 for holding/positioning a specimen 13. The vacuum chamber 7 is evacuated using vacuum pumps (not depicted). With the aid of voltage source 15, the specimen holder 9, or at least the specimen 13, may, if desired, be biased (floated) to an electrical potential with respect to ground.

The particle-optical column 3 comprises an electron source 17 (such as a Schottky emitter), (electrostatic/magnetic) lenses 19, 21 (in general, more complex in structure than the schematic depiction here) to focus the electron beam 5 onto the specimen 13, and a deflection unit 23 to perform beam deflection/scanning of the beam 5. When the beam 5 impinges on/is scanned across the specimen 13, it will precipitate emission of various types of "stimulated" radiation, such as backscattered electrons, secondary electrons, X-rays and cathodoluminescence (infra-red, visible and/or ultra-violet photons); one or more of these radiation types can then be sensed/recorded using one or more detectors, which may form an image, spectrum, diffractogram, etc., typically by assembling a "map" (or "matrix") of detector output as a function of scan position on the specimen. The present Figure shows two such detectors, 25, 27, which may, for example, be embodied as follows:

Detector 25 may, for example, be an electron detector (such as an Solid State Photo-Multiplier), X-ray detector (such as an SDD or Si(Li) sensor) or a light detector (such as a photodiode).

Detector 27 is a segmented electron detector, comprising a plurality of independent detection segments (e.g. quadrants) disposed about a central aperture 29 (allowing passage of the beam 5). Such a detector can, for example, be used to investigate (the angular dependence of) a flux of output (secondary or backscattered) electrons emerging from the specimen 13.

These are just examples, and the skilled artisan will understand that other detector types, numbers and geometries/configurations are possible.

The microscope 1 further comprises a controller/computer processing unit 31. The controller includes a non-transitory memory for storing computer readable instructions and a processor for executing the instructions. By executing the computer readable instructions, the microscope is configured to implement the methods disclosed herein. For example, the controller is configured to control inter alia the lenses 19 and 21, the deflection unit 23, and detectors 25, 27, and display information gathered from the detectors 25, 27 on a display unit 33 (such as a flat panel display), wherein such control occurs via control lines (buses) 31'. The controller 31 (or another controller) can additionally be used to perform various mathematical processing, such as combining, integrating, subtracting, false colouring, edge enhancing, and other processing known to the skilled artisan. In addition, automated recognition processes (e.g. as used for particle analysis) may be included in such processing.

Also depicted is a vacuum port 7', which may be opened so as to introduce/remove items (components, specimens) to/from the interior of vacuum chamber 7, or onto which, for example, an ancillary device/module may be mounted (not depicted). A microscope 1 may comprise a plurality of such ports 7', if desired.

Figure 6:
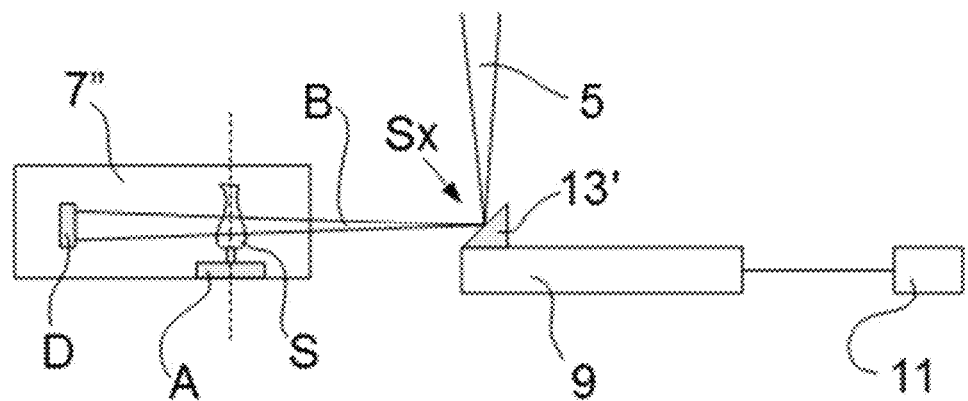
FIG. 6 illustrates a CT module suitable for use in a CPM such as that shown in FIG. 5.

In the context of the current invention, the microscope 1 can also comprise an in situ CT module 7" as shown in FIG. 6. In this figure, the CPM's specimen holder 9 has been provided with a metal target 13', which is positioned (using actuator 11) so that electron beam 5 impinges upon it, thus producing Bremsstrahlung X-rays in a variety of directions. The Figure shows a beam B of such X-rays that propagate to one side from target 13' (effective source Sx) into module 7", where they pass through a specimen S and impinge upon a detector D: compare to FIG. 1. The specimen S is mounted on a stage apparatus A that allows the specimen S to be positioned/moved (typically translated and rotated) relative to the source Sx.

Such a CT module 7" may be permanently present (ab initio) in the vacuum enclosure 7, or it may be an add-on module that can be mounted (post-manufacture of the CPM 1) on/within a spare vacuum port 7', for example.

The invention claimed is:

1. A method of investigating a specimen (S) using tomographic imaging, comprising:
   Providing a specimen (S) and a source (Sx);
   Directing a beam (B) of radiation from said source (Sx) to said specimen (S);
   Detecting a flux of radiation transmitted through said specimen (S);
   Moving at least one of said specimen (S) and said source (Sx) for providing relative motion of the source (Sx) with respect to the specimen (S); and
   Imaging the specimen (S) along a series of different viewing axes (Vi), which intersect a virtual reference surface (Sr) that surrounds the specimen and is substantially centered thereon, wherein said combined steps of moving and imaging generate a sampling geometry (Gs) on said virtual reference surface (Sr);
   Characterized in that said steps of moving and imaging are coordinated in such a way that said sampling geometry (Gs) comprises a plurality of spaced apart line segments (Ls).

2. Method according to claim 1, wherein said plurality of spaced apart line segments (Ls) comprise a first line segment (Ls1) and a second line segment (Ls2) spaced apart from said first line segment (Ls1).

3. Method according to claim 1, comprising the step of continuously imaging at least one of said plurality of spaced apart line segments (Ls).

4. Method according to claim 1, comprising the step of discontinuing imaging in between said plurality of spaced apart line segments (Ls).

5. Method according to claim 1, wherein said sampling geometry (Gs) comprises an array (AL) of said spaced apart line segments (Ls).

6. Method according to claim 5, wherein said array (AL) consists of a regular grid of spaced apart line segments (Ls).

7. Method according to claim 1, wherein said step of moving comprises combined movement in a longitudinal (z) direction and in a tangential (θ) direction.

8. Method according to claim 7, wherein sequential spaced apart line segments (Ls) exhibit a continuity in said longitudinal direction.

9. Method according to claim 7, wherein sequential spaced apart line segments (Ls) exhibit a discontinuity in said tangential direction.

10. Method according to claim 9, wherein said discontinuity corresponds with a tangential rotation between 30-90°.

11. Method according to claim 9, wherein said discontinuity corresponds with a tangential rotation between 45-75°.

12. Method according to claim 7, wherein, for a single line segment (Ls), said movement in said longitudinal direction is ranged in between 1-5% of total sample height.

13. Method according to claim 7, wherein, for a single line segment (Ls), said movement in said tangential direction is ranged in between 5-25°.

14. A tomographic imaging apparatus comprising:
   A specimen holder, for holding the specimen (S);
   A source (Sx), for producing a beam (B) of radiation that can be directed at the specimen (S);
   A detector (D), for detecting a flux of radiation transmitted through the specimen (S) from the source (Sx);
   A stage apparatus (A), for producing relative motion of the source (Sx) with respect to the specimen (S),
   A controller includes a processor, by executing computer readable instructions with the processor, said tomographic imaging apparatus is configured to:
   Direct said beam (B) of radiation from said source (Sx) to said specimen (S);
   Move at least one of said specimen (S) and said source (Sx); and
   Image said specimen (S) along a series of different viewing axes (Vi), said viewing axes intersect a virtual reference surface (Sr) that surrounds the specimen and is substantially centered thereon, said combined steps of moving and imaging generating a sampling geometry (Gs) comprising a plurality of spaced apart line segments (Ls) on said virtual reference surface (Sr).

15. The tomographic imaging apparatus of claim 14, wherein said viewing axes intersects said virtual reference surface at a plurality of intersection points, and the line segments are formed by the plurality of intersection points, wherein a distance between adjacent intersection points within each line segment is shorter than a distance between intersection points from adjacent line segments on said virtual reference surface.

16. The tomographic imaging apparatus of claim 14, wherein said tomographic imaging apparatus is configured to continuously imaging at least one of said plurality of spaced apart line segments.

17. The tomographic imaging apparatus of claim 14, wherein moving at least one of said specimen and said source includes combined movement in a longitudinal (z) direction and in a tangential (θ) direction.

18. The tomographic imaging apparatus of claim 17, wherein sequential spaced apart line segments exhibit a discontinuity in a tangential rotation between 30-90°.

19. The tomographic imaging apparatus of claim 17, wherein for a single line segment, said movement in said longitudinal direction is ranged in between 1-5% of total sample height.

20. A charged-particle microscope, comprising a tomographic imaging apparatus according to claim 14.

* * * * *